United States Patent
Joshi et al.

(10) Patent No.: US 10,821,087 B2
(45) Date of Patent: Nov. 3, 2020

(54) STABILIZED INJECTABLE EMULSION OF PROPOFOL AND KETAMINE

(71) Applicant: NEON LABORATORIES LIMITED, Mumbai (IN)

(72) Inventors: Neeta Joshi, Mumbai (IN); Mangesh Kahane, Mumbai (IN)

(73) Assignee: NEON LABORATORIES LIMITED, Mumbai (IN)

( * ) Notice: Subject to any disclaimer, the term of this patent is extended or adjusted under 35 U.S.C. 154(b) by 76 days.

(21) Appl. No.: 16/095,136

(22) PCT Filed: Apr. 1, 2016

(86) PCT No.: PCT/IN2016/050103
§ 371 (c)(1),
(2) Date: Oct. 19, 2018

(87) PCT Pub. No.: WO2017/017693
PCT Pub. Date: Feb. 2, 2017

(65) Prior Publication Data
US 2019/0133970 A1 May 9, 2019

(30) Foreign Application Priority Data

Jul. 24, 2015 (IN) .................. 2829/MUM/2015

(51) Int. Cl.
| | | |
|---|---|---|
| *A61K 31/135* | (2006.01) | |
| *A61K 31/05* | (2006.01) | |
| *A61K 9/107* | (2006.01) | |
| *A61K 47/14* | (2017.01) | |
| *A61K 9/00* | (2006.01) | |
| *A61K 47/24* | (2006.01) | |
| *A61K 47/18* | (2017.01) | |
| *A61K 47/44* | (2017.01) | |
| *A61K 47/02* | (2006.01) | |

(52) U.S. Cl.
CPC .......... *A61K 31/135* (2013.01); *A61K 9/0019* (2013.01); *A61K 9/107* (2013.01); *A61K 31/05* (2013.01); *A61K 47/183* (2013.01); *A61K 47/24* (2013.01); *A61K 47/44* (2013.01); *A61K 47/02* (2013.01)

(58) Field of Classification Search
CPC ...... A61K 9/0019; A61K 9/107; A61K 31/05; A61K 31/135; A61K 47/24
See application file for complete search history.

(56) References Cited

U.S. PATENT DOCUMENTS

| | | | |
|---|---|---|---|
| 6,399,087 B1 * | 6/2002 | Zhang | A61K 9/0019 424/405 |
| 6,469,069 B1 | 10/2002 | Mirejovsky et al. | |
| 2011/0046116 A1 | 2/2011 | Cukrowski | |

FOREIGN PATENT DOCUMENTS

| | | |
|---|---|---|
| CN | 1331582 A | 1/2002 |
| CN | 1626081 A | 6/2005 |
| CN | 1628665 A | 6/2005 |
| CN | 1660094 A | 8/2005 |
| CN | 102038651 A | 5/2011 |
| CN | 102552126 A | 7/2012 |
| CN | 102670489 A | 9/2012 |
| EP | 1163007 B1 | 5/2003 |
| EP | 0821588 B1 | 6/2003 |
| EP | 2450039 A1 | 5/2012 |
| WO | WO 00/10531 | 3/2000 |
| WO | WO 2004/108113 A1 | 12/2004 |
| WO | WO-2004108113 A1 * | 12/2004 ............. A61K 31/05 |

OTHER PUBLICATIONS

"International Search Report and Written Opinion for", PCT/IN2016/050100 dated Sep. 7, 2016.
Bahadur, et al., "Sedation with Combination of Midazolam, Pentazocine and Propofol for Colonoscopy in Outdoor Patients", MJSBH Jul.-Dec. 2012, vol. 11, Issue 2, pp. 7-9.
Dar, et al., "Evaluation of Hyperbaric Spinal Ropivacaine in Lower Limb and Hip Surgery: A Comparison with Hyperbaric Bupivacaine", American Journal of Advanced Drug Delivery, 8 pages, Nov. 28, 2013.
Koo, et al., "Small-Dose Ketamine Reduces the Pain of Propofol Injection", International Anesthesia Research Society, vol. 103, No. 6, Dec. 2006, pp. 1444-1447.
Luck, "Spinal Anaesthesia for elective surgery: a comparison of hyperbaric solutions of racemic bupivacaine, levobupivacaine, and ropivacaine", British Journal of Anaesthesia 101 (5): 705-10 (2008).
Vimolluck, et al., "Clinical Characteristics of Spinal Levobupivacaine: Hyperbaric Compared with Isobaric Solution", The Scientific World Journal, vol. 2012, Article ID 169076, 7 pages, Oct. 26, 2011.

* cited by examiner

*Primary Examiner* — Theodore R. West
(74) *Attorney, Agent, or Firm* — Kramer Amado, P.C.

(57) ABSTRACT

Disclosed herein is stable injectable emulsion of Propofol and Ketamine in combination; a base to adjust the pH and purified Lecithin.

13 Claims, No Drawings

STABILIZED INJECTABLE EMULSION OF PROPOFOL AND KETAMINE

TECHNICAL FIELD

The present invention provides highly stabilized injectable emulsion of Propofol and Ketamine. The invention provides injectable emulsion comprising of Propofol; Ketamine; emulsifier, Chelating agent, and pH adjuster with water as principle solvent. The invention further relates to process of preparation of stable injectable emulsion of Propofol and Ketamine in combination.

BACKGROUND AND PRIOR ART

Ketamine was developed in the 1960s as a safer and more predictable anaesthetic than its precursor phencyclidine (PCP). It is a unique agent in procedural sedation and analgesia (PSA) in that it is a "dissociative" anaesthetic that functions by blocking communication between the thalamic and limbic regions of the brain, thereby preventing the brain from processing external stimuli.

In chemical structure, Ketamine is an aryl Cyclohexylamine derivative. Ketamine is a chiral compound. Most pharmaceutical preparations of Ketamine are racemic; however, some brands reportedly have differences in their enantiomeric proportions.

Propofol is a non-barbiturate sedative hypnotic developed in Europe in the 1970s. Its popularity as a PSA agent is growing rapidly due mainly to its favourable pharmacokinetic profile as the lipid solubility confers a quick onset and short recovery time. It also has the advantages of functioning as an antiemetic, an anticonvulsant, and an amnestic agent. Propofol is a popular IV anaesthetic induction drug that causes pain, so to reduce the pain the propofol will be co-administered with a local anaesthetic agent. Lidocaine is commonly used to decrease injection-related pain with Propofol injection.

The currently available Propofol preparation comprises 1% Propofol, 10% soybean oil, and 1.2% purified egg phospholipids as an emulsifier, with 2.25% glycerol as a tonicity-adjusting agent, and sodium hydroxide to adjust the pH.

Ketamine (a phencyclidine derivative) has potent analgesic effects and local anesthetic properties. It seems likely that the reduction in Propofol injection pain was the result of a peripheral action which attenuated the afferent pain pathways Ketamine as a NMDA receptor antagonist may activate these receptors either in the vascular endothelium or in the central nervous system It is postulated that by combining these two agents for PSA may preserve sedation efficacy while minimizing their respective adverse effects. This is due partly to the fact that many of the aforementioned potential adverse effects are dose-dependent, and when used in combination the doses administered of each can be reduced. Also, the cardiovascular effects of each are opposing in action, thus theoretically balancing each other out when used together.

The mixture of Ketamine and Propofol administered together is reportedly an effective agent for procedural sedation and analgesia in the emergency department.

This combination has also been shown to be safe and effective in the operating room and the ICU setting and as an induction agent for rapid-sequence intubation in the emergency department. The combination of Ketamine and Propofol appears to provide sedation and analgesia with fewer toxic effects than either drug alone and with fewer adverse effects than the combination of Propofol and Fentanyl.

U.S. Pat. Nos. 6,399,087, 6,469,069, CN1331582T, WO0010531, EP1,163,007 contains various cloudy emulsions containing Propofol like drugs and various patents are cited to improve such emulsion composition either for stable homogenized formulation or for its stability against microorganisms by use of addition of EDTA or addition of sulphite.

WO 2004108113A1 discloses a clear, stable, ready to use anaesthetic composition comprising Propofol. At least one analgesic and like drug and antioxidants in a solvent system and a process for preparing the same. The said solvent system is selected from water and 2,5 di-omethyl-1,4;3,6-dianhydro-D-glucitol and/or its derivatives in the ratio of 65:35 and cyclodextrin and its derivative and water, wherein cyclodextrin forms a complex with Propofol in a ratio of 1:1. The analgesic is selected from Lignocaine, Ketamine, Tramodol, Alfentanil, Pethidine, Ropivacaine, Bupivacaine, Ketamine and the like capable of being administered parenterally wherein ratio of Propofol:Lignocaine is 100:1 and Propofol:Ketamine is 100:5. The process for preparing the anaesthetic composition comprises mixing Propofol in solvent system for effective dissolution of Propofol followed by addition of analgesic agents and further addition of antioxidants in the desired quantity and mixing, adjusting the pH, filtering the mixture and filling in multidose vials.

Ketamine is a useful drug in anesthetic practice in that it produces sedation, amnesia, and profound analgesia. Its use in ambulatory surgery has been limited because of the potential for postoperative hallucinations, dissociative reactions, and delayed recovery. Recent studies have demonstrated that the co-administration of Propofol and Ketamine prevents Ketamine induced psychic disturbances. The comparative efficacy and side effects of Propofol in combination with Ketamine to Propofol alone for intravenous sedation during laparoscopic tubal ligation is reported by Ravindra V. Prasad, et. al in an article titled "Ketamine and Propofol in combination for sedation during laparoscopic tubal ligation"

Findings suggest that a dose of 100 µg/kg Ketamine administered just before Propofol can reduce the incidence and intensity of Propofol induced pain without significant adverse hemodynamic effects. (Jai-Hyun Hwang, M D "Small-Dose Ketamine Reduces the Pain of Propofol Injection" International anaesthesia Research Society, Vol. 103, No. 6, Page No. 1444-1447). Although co-administration of Ketamine and Propofol for procedural sedation and analgesia theoretically may be beneficial, however, reports relating to compatibility data for the two agents combined in a syringe are not available. The available evidence does not support the use of a fixed-dose ketamine-propofol combination for procedural sedation and analgesia.

In view of the above, it is evident that there is long standing need in the art to provide Combination of Propofol and Ketamine together in injectable emulsion form with low impurity profile.

Therefore, the object of the invention is to provide a stable injectable emulsion of Propofol and Ketamine in combination with low impurity profile and thus to have long therapeutic stability.

DETAILED DESCRIPTION OF THE INVENTION

In accordance with the objective, the invention provides stable injectable emulsion of Propofol and Ketamine in combination.

Ketamine has potent analgesic and local anesthetic properties; Propofol is a popular IV anaesthetic induction drug that causes pain so to reduce the pain Propofol can be given in combination with ketamine. Therefore, the main rational of the present invention is to provide a formulation of stable injectable emulsion of Propofol and Ketamine in combination that gives less/no pain on administration.

Propofol in higher dose causes cardio-respiratory depressant effects, so in an attempt to reduce Propofol adverse cardio-respiratory depressant effects, the combined use of Propofol and Ketamine has been proposed in the instant invention.

IV injection of Propofol during anesthetic induction induces pain and by using Ketamine it has been proposed to reduce injection pain according to the present invention.

The currently marketed formulation of Propofol is an opaque oil-in-Water emulsion containing lipids and egg lecithin as an emulsifying agent. The emulsion-type formulation contains Propofol, soybean oil, glycerol, egg lecithin and disodium edetate (EDTA) at a pH of 7.0 to 8.5.

According to an embodiment of the present invention, Propofol may be dissolved in a pharmaceutically acceptable water immiscible solvent and emulsified in water and said emulsion is stabilized by means of a surfactant. In an alternate embodiment, Propofol may itself be emulsified in water without addition of a water immiscible solvent and said emulsion stabilized by means of a surfactant/emulsifier.

Typical dosages of Propofol for Parenteral administration are 0.33 mg/kg/h, but may range up to 10 mg/kg/h in exceptional cases, which is equivalent to 1.68 L emulsion/day/70 kg.

Water immiscible solvents suitable for the preparation of oil in water emulsions suitable for parenteral administration are known to those skilled in the pharmaceutical arts. Typically, the water immiscible solvent that also acts as an emulsifier will be a vegetable oil: for example, soybean, safflower, cottonseed, corn, sunflower, *Arachis*, and castor. The water immiscible solvent may also be a wholly or partially manufactured material, for Example mono, di, and triglycerides, fatty acid esters, or chemically and/or physically modified vegetable oils.

The composition according to the invention may comprise Propofol and Ketamine in a ratio of 1:0.5 to 1:10.

Accordingly, in various embodiments, the composition of the present invention comprises Propofol and Ketamine in a ratio of, for example 1:0.5, 1:1, 1:2, 1:3 and the like.

The injectable emulsion of Propofol and Ketamine in combination provided according to the invention comprises 0.3 to 2.3% w/v; more preferably, 1.0 to 1.5% w/v of Purified lecithin to increase the purity and stability of formulation.

In an embodiment, injectable emulsion of Propofol and Ketamine in combination comprises 1.0 to 1.5% w/v of Purified lecithin.

In an embodiment, the injectable emulsion of Propofol and Ketamine combination comprises a chelating agent, i.e dosodium edetate and a solubilizer like glycerol. In a preferred embodiment, the stable injectable emulsion of Propofol and Ketamine in combination consists of Sodium hydroxide to adjust the pH and Water as principle solvent.

According to preferred embodiment, the pH of the stable injectable emulsion of Propofol and Ketamine in combination is adjusted with Sodium hydroxide. The pH of stable injectable emulsion is preferably between 3.0 & 6.0.

In another embodiment, the invention provides a process for preparation of stable injectable emulsion of Propofol and Ketamine in combination which comprises;

a. Dissolving Disodium E.D.T.A., & mixing Glycerol in part of water for Injection;

b. In a suitable capacity & dry container taken Soybean Oil;

c. Adding & dissolving Purified lecithin in Soy bean oil under stirring to dissolve completely;

d. Adding & mixing Propofol to the contents of step (c) under stirring and homogenise above solution to obtain an emulsion;

e. Adding & dissolving Ketamine Hydrochloride in water for Injection of step (a) followed by addition of the contents of step (e) to step (d);

f. Making up the volume with Water for Injection and homogenised the emulsion & checking the pH.

The injectable emulsion of Propofol and Ketamine in combination consists of 0.3 to 2.3% w/v of Purified lecithin.

In an embodiment, injectable emulsion of Propofol and Ketamine in combination consists of 1.0 to 1.5% w/v of Purified lecithin.

Several compositions were prepared & tested for stability. Some of these trials are discussed below in brief.

The following examples, which include preferred embodiments, will serve to illustrate the practice of this invention, it being understood that the particulars shown are by way of examples and for purpose of illustrative discussion of preferred embodiments of the invention.

Example 1

| Sr. No. | Ingredients | Quantity/mL |
| --- | --- | --- |
| 1. | Propofol | 10 mg |
| 2. | Ketamine Hydrochloride | 5 mg |
| 3. | Purified lecithin, Soybean oil, Glycerol, Disodium E.D.T.A. | Q.S |
| 4. | Sodium Hydroxide | Q.S for pH Adjustment |
| 5. | Water for injection | Q.S to 1 mL |

Procedure:

a. Dissolving Disodium E.D.T.A., & mixing Glycerol in part of water for Injection;

b. In a suitable capacity & dry container taken Soybean Oil;

c. Adding & dissolving Purified lecithin in Soy bean oil under stirring to dissolve completely;

d. Adding & mixing Propofol to the contents of step (c) under stirring to homogenise above solution to obtain an emulsion;

e. Adding & dissolving Ketamine Hydrochloride in water for Injection of step (a) followed by addition of the contents of step (e) to step (d);

f. Making up the volume with Water for injection and homogenised the emulsion & checking the pH.

The results are discussed in table 1 herein below:

| Stage | Assay Propofol | Assay Ketamine | pH | Lysolecithin (By HPLC) N.M.T. 0.2% w/v of Propofol | Propofol quinone & Propofol dimer (By HPLC) Propofol quinone (Imp. J) N.M.T. 0.1% |
|---|---|---|---|---|---|
| Initial | 104.26% | 103.50% | 4.02 | 0.016% | 0.0103% |
| 1 M/25° C. | 101.84% | 101.10% | 4.89 | 0.037% | 0.0030% |
| 1 M/40° C. | 101.51% | 101.50% | 4.95 | 0.023% | 0.006% |
| 2 M/25° C. | 101.84% | 101.51% | 4.91 | 0.056% | 0.003% |
| 2 M/40° C. | 101.51% | 99.95% | 4.93 | 0.065% | 0.008% |
| 3 M/25° C. | 102.91% | 101.89% | 4.92 | 0.018% | 0.001% |
| 3 M/40° C. | 99.90% | 99.12% | 4.93 | 0.027% | 0.001% |

Example 2

| Sr. No. | Ingredients | Quantity/mL |
|---|---|---|
| 1. | Propofol | 10 mg |
| 2. | Ketamine Hydrochloride | 10 mg |
| 3. | Purified lecithin, Soybean oil, Glycerol, Disodium E.D.T.A. | Q.S |
| 4. | Sodium Hydroxide | Q.S for pH Adjustment |
| 5. | Water for injection | Q.S to 1 mL |

Procedure:
a. Dissolving Disodium E.D.T.A., & mixing Glycerol in part of water for Injection;
b. In a suitable capacity & dry container taken Soybean Oil;
c. Adding & dissolving Purified lecithin in Soy bean Oil under stirring to dissolve completely;
d. Adding & mixing Propofol to the contents of step (c) under stirring to homogenise above solution to obtain an emulsion;
e. Adding & dissolving Ketamine Hydrochloride in water for Injection of step (a) followed by addition of the contents of step (e) to step (d);
f. Making up the volume with Water for injection and homogenised the complete emulsion & checking the pH.

The results are discussed in table 2 herein below:

| Stage | Assay Propofol | Assay Ketamine | pH | Lysolecithin (By HPLC) N.M.T. 0.2% w/v of Propofol | Propofol quinone & Propofol dimer (By HPLC) Propofol quinone (Imp. J) N.M.T. 0.1% |
|---|---|---|---|---|---|
| Initial | 100.49% | 100.45% | 5.41 | 0.15% | 0.02% |
| 1 M/25° C. | 100.48% | 101.80% | 5.26 | 0.14% | 0.01% |
| 1 M/40° C. | 99.56% | 99.99% | 5.29 | 0.15% | 0.015% |
| 2 M/25° C. | 101.35% | 100.20% | 5.21 | 0.13% | 0.014% |
| 2 M/40° C. | 100.85% | 100.26% | 5.23 | 0.14% | 0.015% |

Example 3

| Sr. No. | Ingredients | Quantity/mL |
|---|---|---|
| 1. | Propofol | 10 mg |
| 2. | Ketamine Hydrochloride | 20 mg |
| 3. | Purified lecithin, Soybean oil, Glycerol, Disodium E.D.T.A. | Q.S |
| 4. | Sodium Hydroxide | Q.S for pH Adjustment |
| 5. | Water for injection | Q.S to 1 mL |

Procedure:
a. Dissolving Disodium E.D.T.A., & mixing Glycerol in part of water for Injection;
b. In a suitable capacity & dry container taken Soybean Oil;
c. Adding & dissolving Purified lecithin in Soy bean oil under stirring to dissolve completely;
d. Adding & mixing Propofol to the contents of step (c) under stirring to homogenise above solution to obtain an emulsion;
e. Adding & dissolving Ketamine Hydrochloride in water for Injection of step (a) followed by addition of the contents of step (e) to step (d);
f. Making up the volume with Water for injection and homogenised the complete emulsion & checking the pH.

The results are discussed in table 3 herein below:

| Stage | Assay Propofol | Assay Ketamine | pH | Lysolecithin (By HPLC) N.M.T. 0.2% w/v of Propofol | Propofol quinone & Propofol dimer (By HPLC) Propofol quinone (Imp. J) N.M.T. 0.1% |
|---|---|---|---|---|---|
| Initial | 99.49% | 100.45% | 5.90 | 0.18% | 0.03% |
| 1 M/25° C. | 98.32% | 99.76% | 5.95 | 0.16% | 0.02% |
| 1 M/40° C. | 98.56% | 98.99% | 5.78 | 0.12% | 0.019% |
| 2 M/25° C. | 97.21% | 97.81% | 5.56 | 0.11% | 0.024% |
| 2 M/40° C. | 97.01% | 97.21% | 5.74 | 0.18% | 0.014% |

Example 4

| Sr. No. | Ingredients | Quantity/mL |
|---|---|---|
| 1. | Propofol | 10 mg |
| 2. | Ketamine Hydrochloride | 30 mg |
| 3. | Purified lecithin, Soybean oil, Glycerol, Disodium E.D.T.A. | Q.S |
| 4. | Sodium Hydroxide | Q.S for pH Adjustment |
| 5. | Water for injection | Q.S to 1 mL |

Procedure:
a. Dissolving Disodium E.D.T.A., & mixing Glycerol in part of water for Injection;
b. In a suitable capacity & dry container taken Soybean Oil;
c. Adding & dissolving Purified lecithin in Soy bean oil under stirring to dissolve completely;
d. Adding & mixing Propofol to the contents of step (c) under stirring to homogenise above solution to obtain an emulsion;
e. Adding & dissolving Ketamine Hydrochloride in water for Injection of step (a) followed by addition of the contents of step (e) to step (d);
f. Making up the volume with Water for injection and homogenised the complete emulsion & checking the pH.

The results are discussed in table 4 herein below:

| Stage | Assay Propofol | Assay Ketamine | pH | Lysolecithin (By HPLC) N.M.T. 0.2% w/v of Propofol | Propofol quinone & Propofol dimer (By HPLC) Propofol quinone (Imp. J) N.M.T. 0.1% |
|---|---|---|---|---|---|
| Initial | 101.87% | 100.65% | 5.87 | 0.09% | 0.07% |
| 1 M/25° C. | 100.98% | 100.01% | 5.65 | 0.08% | 0.02% |
| 1 M/40° C. | 99.86% | 99.54% | 5.45 | 0.12% | 0.078% |
| 2 M/25° C. | 99.64% | 99.13% | 5.78 | 0.07% | 0.056% |
| 2 M/40° C. | 98.65% | 98.64% | 5.90 | 0.15% | 0.023% |

We claim:

1. An injectable emulsion of propofol and ketamine, comprising:
   a) a combination of propofol and ketamine in a ratio ranging from 1:0.5 to 1:10;
   b) a pH adjuster; and
   c) lecithin.

2. The injectable emulsion according to claim 1, wherein the pH adjuster is a base.

3. The injectable emulsion according to claim 2, wherein the base is sodium hydroxide.

4. The injectable emulsion according to claim 1, wherein the composition comprises between 0.3% w/v and 2.3% w/v of lecithin.

5. The injectable emulsion according to claim 4, wherein the composition comprises between 1.0% w/v and 1.5% w/v of lecithin.

6. The injectable emulsion according to claim 1, wherein the emulsion has a pH between 3.0 and 6.0.

7. An injectable emulsion of propofol and ketamine, comprising:
   a) a combination of propofol and ketamine in a ratio ranging from 1:0.5 to 1:10;
   b) a pH adjuster; and
   c) lecithin;
   wherein the concentration of propofol and the concentration of ketamine is essentially unchanged after storage for up to two months at a temperature of 25° C. to 40° C.

8. A process for preparation of an injectable emulsion of propofol and ketamine, comprising:
   a) dissolving disodium E.D.T.A. in a mixture of water and glycerol;
   b) dissolving lecithin in soybean oil with stirring to obtain a lecithin solution;
   c) mixing propofol with the lecithin solution with stirring to obtain a propofol emulsion;
   d) dissolving a ketamine salt in water to obtain a ketamine solution followed by addition of the ketamine solution to the propofol emulsion to obtain an emulsion of propofol and ketamine;
   e) homogenising the emulsion of propofol and ketamine, and thereby
   f) obtaining the injectable emulsion of claim 1.

9. The process according to claim 8, wherein the homogenised emulsion has a pH of between 3.0 and 6.0.

10. The process according to claim 8, wherein the homogenised emulsion comprises 1.0% w/v to 1.5% w/v of lecithin.

11. The process according to claim 8, further comprising a step of adding sufficient water to the emulsion of propofol and ketamine to obtain a desired volume of the emulsion.

12. The process according to claim 11, wherein the step of adding water to the emulsion of propofol and ketamine is carried out prior to homogenising the emulsion.

13. The process according to claim 8, further comprising a step of adjusting the pH of the emulsion of propofol and ketamine to between 3.0 and 6.0 with a pH adjuster.

* * * * *